United States Patent
Baek

(10) Patent No.: US 10,842,905 B2
(45) Date of Patent: Nov. 24, 2020

(54) AIR STERILIZER

(71) Applicant: SMI CO., LTD., Chuncheon-si (KR)

(72) Inventor: Myung Soo Baek, Chuncheon-si (KR)

(73) Assignee: SMI CO., LTD., Chuncheon-si (KR)

( * ) Notice: Subject to any disclaimer, the term of this patent is extended or adjusted under 35 U.S.C. 154(b) by 85 days.

(21) Appl. No.: 16/203,361

(22) Filed: Nov. 28, 2018

(65) Prior Publication Data

US 2019/0175779 A1    Jun. 13, 2019

(30) Foreign Application Priority Data

Dec. 11, 2017    (KR) .......................... 10-2017-0169220

(51) Int. Cl.
| | |
|---|---|
| *A61L 9/00* | (2006.01) |
| *A61L 9/18* | (2006.01) |
| *A61L 9/22* | (2006.01) |
| *B01D 46/00* | (2006.01) |
| *B01D 46/10* | (2006.01) |
| *B01D 46/12* | (2006.01) |

(52) U.S. Cl.
CPC .................. *A61L 9/18* (2013.01); *A61L 9/22* (2013.01); *A61L 2202/25* (2013.01); *A61L 2209/14* (2013.01); *A61L 2209/15* (2013.01)

(58) Field of Classification Search
CPC ..... A61L 9/00; A61L 9/16; A61L 9/18; A61L 9/22; A61L 2209/00; A61L 2209/10; A61L 2209/13; A61L 2209/134; A61L 2209/14; A61L 2209/15; B01D 46/00; B01D 46/10; B01D 46/12
See application file for complete search history.

(56) References Cited

U.S. PATENT DOCUMENTS

| | | | | |
|---|---|---|---|---|
| 4,253,852 | A * | 3/1981 | Adams | .................. B03C 3/09 |
| | | | | 361/230 |
| 2003/0010211 | A1* | 1/2003 | Yu | .......................... B03C 3/155 |
| | | | | 96/16 |

FOREIGN PATENT DOCUMENTS

| | | |
|---|---|---|
| JP | 2003-157953 A | 5/2003 |
| KR | 10-2005-0115398 A | 12/2005 |

(Continued)

OTHER PUBLICATIONS

Machine translation of KR 2016-0097816 A, which was published on Aug. 18, 2016 (Year: 2016).*

(Continued)

*Primary Examiner* — Natasha E Young
(74) *Attorney, Agent, or Firm* — Rabin & Berdo, P.C.

(57) ABSTRACT

Provided is an air sterilizer for filtering and discharging harmful components from inflowing air, comprising: a body having an air inlet part, through which outside air is introduced, and an air outlet part, through which the air filtered inside is discharged; a primary filtering part detachably provided in the body and filtering contaminant particles from the inflowing and moving air; an air intake fan for allowing the air to inflow through the air inlet part; a secondary electrostatic filter part for sterilizing harmful components from the air, which has been filtered through the primary filtering part, by applying continuous and repetitive damage to the harmful components; and an ion-generating part for supplying anions to the air, from which the harmful components have been filtered through the secondary electrostatic filter part, so as to allow the air to be discharged to the outside.

2 Claims, 6 Drawing Sheets

(56) References Cited

FOREIGN PATENT DOCUMENTS

| KR | 10-0573391 | B1 |   | 4/2006 |
|----|------------|----|---|--------|
| KR | 10-0704433 | B1 |   | 4/2007 |
| KR | 10-1434751 | B1 |   | 8/2014 |
| KR | 20160097816 | A | * | 8/2016 |
| TW | M496739 | U | * | 3/2015 |

OTHER PUBLICATIONS

Machine translation of TW M96739 U, which was published on Mar. 1, 2015 (Year: 2015).*

* cited by examiner

AIR STERILIZER

CROSS REFERENCE TO RELATED APPLICATIONS

This application is based upon and claims the benefit of priority of Korean Patent Application No. 10-2017-0169220, filed on Dec. 11, 2017, the entire contents of which are incorporated herein by reference.

BACKGROUND OF THE INVENTION

Field of the Invention

The present invention relates to an air sterilizer and, more particularly, to an air sterilizer which is installed in a living space such as a hospital, a hotel, a school, a sports facility, a smoking booth and the like so as to purify and stabilize internal air and maintain clean air.

Background Art

Various pollution sources introduced from the outside are generated in a public place where a lot of people gather, and in the public place, various products having cleaning functions are installed to clean the polluted air and maintain pleasant indoor air.

Especially, in the case of schools, dormitories, hospitals, etc. where many people gather, various types of sterilization devices are installed due to the risk of bacterial infections caused by indoor air as well as food.

As an example, there is an air sterilizer disclosed in Korean Reg. Patent Publication No. 0573391.

This air sterilizer allows the deodorization efficiency to be maximized by giving sufficient time to activate the photocatalyst of air but has a problem in that it takes a considerable time to remove pollution sources.

In addition, Korean Reg. Patent Publication No. 0704433 discloses an air purifier having a disinfecting function.

This air purifier is to disinfect the pathogen adhered to a surrounding structure and the pathogen afloat in the air together by discharging a mixed gas containing disinfectant while purifying air by removing foreign matters contained in the air, but there is a problem that respiratory diseases can be caused due to the discharge of the chemical solution.

Furthermore, Korean Reg. Patent Publication No. 1434751 discloses the air purifier having the disinfecting function, in which the air filtered by a filtering copper plate and a mesh member is sucked into a purifying chamber through a suction port so as to be sterilized by ultraviolet rays and then is exhausted through an exhaust port at the left side so as to clean room air and, at the same time, the air sucked into the purifying chamber and thus sterilized and purified therein is supplied to a lower sterilizing and disinfecting chamber through a downward opening window so as to sterilize a cup and a toothbrush in the sterilizing and disinfecting chamber and then is discharged to a room so as to purify the internal air of the room outside a sterilizer more cleanly. However, the air purifier still has a problem in that harmful components are generated around the device due to purification through the ultraviolet rays.

PRIOR ART DOCUMENTS

Patent Documents (Patent Document 0001) Korean Reg. Patent Publication No. 0573391, Publication Date 25 Apr. 2006

(Patent Document 0002) Korean Reg. Patent Publication No. 0704433, Publication Date 6 Apr. 2007

(Patent Document 0003) Korean Reg. Patent Publication No. 1434751, Publication Date 29 Aug. 2014

SUMMARY OF THE INVENTION

Technical Problem

Accordingly, the present invention has been made to solve the above-mentioned problems occurring in the prior art, and thus the present invention has following objectives.

Firstly, the present invention has an objective to discharge air after sequentially removing various pollution sources several times from the air flowing into a body.

Secondly, the present invention has an objective to sterilize bacteria remaining in a filtering space after air disinfection.

Thirdly, the present invention has an objective to apply repetitive damage to pollution sources during air disinfection, thereby performing the air disinfection more quickly.

Technical Solution

To accomplish the above objectives, the present invention provides an air sterilizer for filtering and discharging harmful components from inflowing air, comprising: a body having an air inlet part, through which outside air is introduced, and an air outlet part, through which the air filtered inside is discharged; a primary filtering part detachably provided in the body and filtering contaminant particles from the inflowing and moving air; an air intake fan for allowing the air to inflow through the air inlet part; a secondary electrostatic filter part for sterilizing harmful components from the air, which has been filtered through the primary filtering part, by applying continuous and repetitive damage to the harmful components; and an ion-generating part for supplying anions to the air, from which the harmful components have been filtered through the secondary electrostatic filter part, so as to allow the air to be discharged to the outside.

The secondary electrostatic filter part may include first and second metal mesh members coupled to each other by means of a frame member so as to face each other up and down and to have a space therebetween, first and second filters positioned in the space between the first and second metal mesh members, and a damage part positioned in a space between the first and second filters so as to apply continuous and repetitive damage to the air passing through the space.

The damage part may include positive and negative electrode members for providing polarities to the first and second metal mesh members, positive and negative needle electrodes positioned between the first and second filters, and a polarity converter for converting the polarities of the positive and negative electrode members by a switching operation.

The ion-generating part may include a rotation fan rotatably coupled to the inside of a case located at the upper side in the space of the body so as to introduce and discharge air, a motor for rotating the rotation fan at one side of the case, and four electrode members arranged in the case and forming electrodes in air so as to generate ions.

Effect of the Invention

The present invention has the following advantages.

Firstly, there is an advantage in discharging inflowing air quickly in a sterilized state, where pollution sources are removed, by applying continuous and repetitive damage to harmful components of the inflowing air.

Secondly, there is an advantage in maintaining a space in a pleasant state by removing external pollution sources by providing anions when discharging the inflowing air in a sterilized state.

Thirdly, there is an advantage in maintaining a filtering space for removing pollution sources from air clean by sterilizing bacteria remaining in the filtering space after air disinfection.

Figure 1:
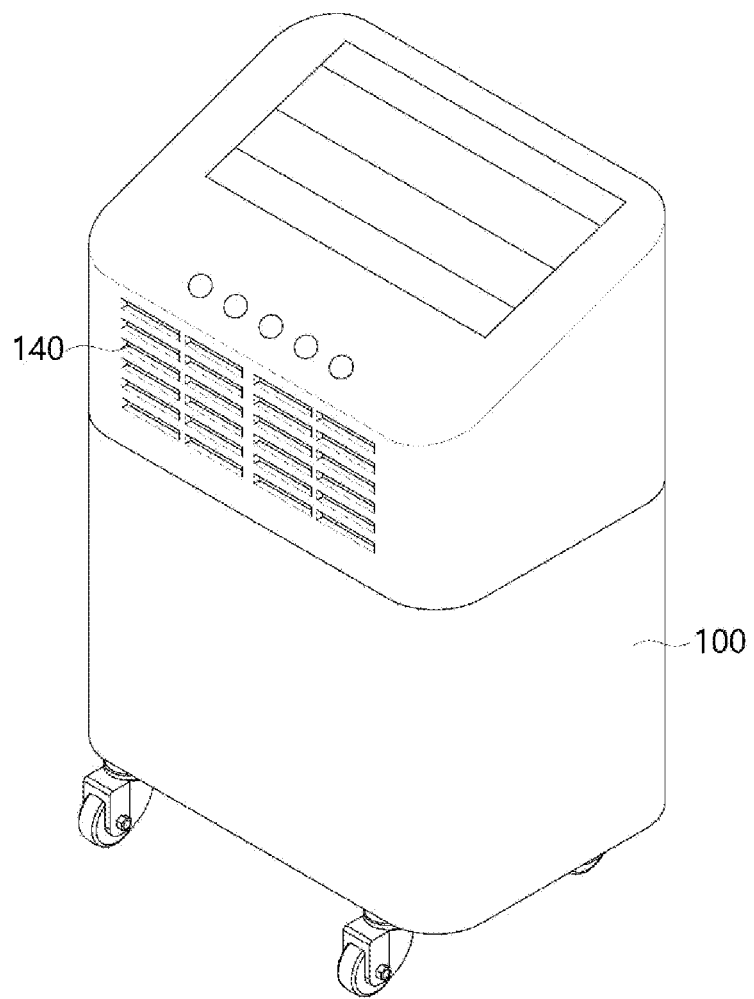
FIG. 1 is a perspective view showing an air sterilizer according to the present invention.

| Brief Explanation of Reference Numerals | |
|---|---|
| 100: body | 110: space |
| 120: air inlet part | 140: air outlet part |
| 200: primary filtering part | |
| 300: air intake fan | |
| 400: secondary electrostatic filter part | |
| 410: first metal mesh member | |
| 420: second metal mesh member | |
| 430: first filter | 440: second filter |
| 450: damage part | |
| 451: positive electrode member | |
| 452: negative electrode member | |
| 453: positive needle electrode | |
| 454: negative needle electrode | |
| 455: polarity converter | |
| 480: frame member | |
| 500: ion-generating part | |
| 510: case | 520: rotation fan |
| 530: motor | 540: electrode member |
| 700: guide means | |

DETAILED DESCRIPTION OF THE PREFERRED EMBODIMENT

Hereinafter, preferred embodiments according to the present invention will be described in detail with reference to the accompanying drawings. In the description of the present invention, if it is determined that related arts and the like can obscure the gist of the present invention, the detailed explanation thereof will be omitted. Hereinafter, an air sterilizer according to the embodiments of the present invention will be described in detail. For purposes of this specification, like reference numerals in the drawings denote like elements unless otherwise indicated.

The present invention relates to an air sterilizer, which discharges inflowing air after sterilizing pollution sources from the inflowing air.

As shown in FIG. 1 to FIG. 7, the air sterilizer according to the present invention includes a body 100 having an air inlet part 120, through which outside air is introduced, and an air outlet part 140, through which the air filtered inside is discharged, a primary filtering part 200 detachably provided in the body 100 and filtering contaminant particles from the inflowing and moving air, an air intake fan 300 for allowing the air to inflow through the air inlet part 120, a secondary electrostatic filter part 400 for sterilizing harmful components from the air, which has been filtered through the primary filtering part 200, by applying continuous and repetitive damage to the harmful components, and an ion generating part 500 for supplying anions to the air, from which the harmful components have been filtered through the secondary electrostatic filter part 400, so as to allow the air to be discharged to the outside.

The body 100 is mounted on the central axis of a support member, which is in close contact with the ground surface, so as to be rotatably coupled thereto and has a space 110 formed therein. The air inlet part 120 is positioned at the lower side of the body 100 such that contaminated air is introduced from the outside through the same, and the air outlet 140 is located at the upper side of the body 100 such that the air disinfected inside the body is discharged to the outside through the same.

The primary filtering part 200 primarily filters harmful components from the air, which has been introduced through the air inlet part 120 and moves upward.

That is, the primary filtering part 200 can be a known HEPA filter and can be detachably coupled to the body 100 in a case form.

The secondary electrostatic filter part 400 includes first and second metal mesh members 410, 420 coupled to each other by means of a frame member so as to face each other up and down and have a space therebetween, first and second filters 430, 440 positioned in the space between the first and second metal mesh members 410, 420, and a damage part 450 positioned in a space between the first and second filters 430, 440 so as to apply continuous and repetitive damage to the air passing through the space.

It is preferable that platinum-plated mesh-like structures are used as the first and second metal mesh members 410, 420, wherein the first and second metal mesh members 410, 420 are spaced from each other in the vertical direction and fixed by a frame member 480 so as to have a space therebetween.

The first and second filters 430, 440 may have the form of a net or a sponge, through which air can pass while foreign matters and the like can be filtered.

Herein, the first and second metal mesh members 410, 420 applied to the secondary electrostatic filter part 400 may be formed as a dual tube in a circular or elliptical shape in addition to the plate shape.

Figure 3:
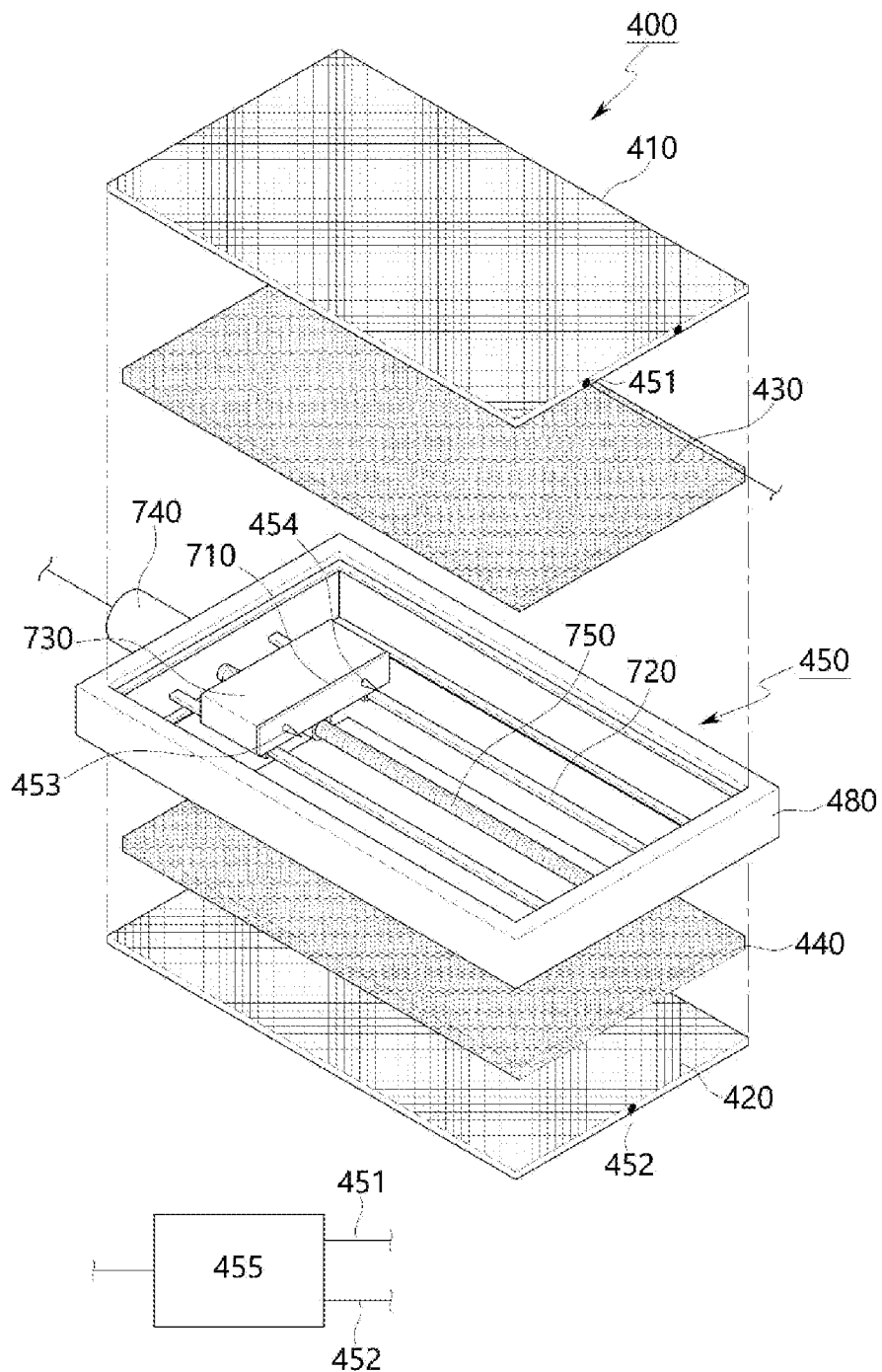
FIG. 3 is an exploded perspective view separately showing a secondary electrostatic filter part shown in FIG. 2.
Figure 4:
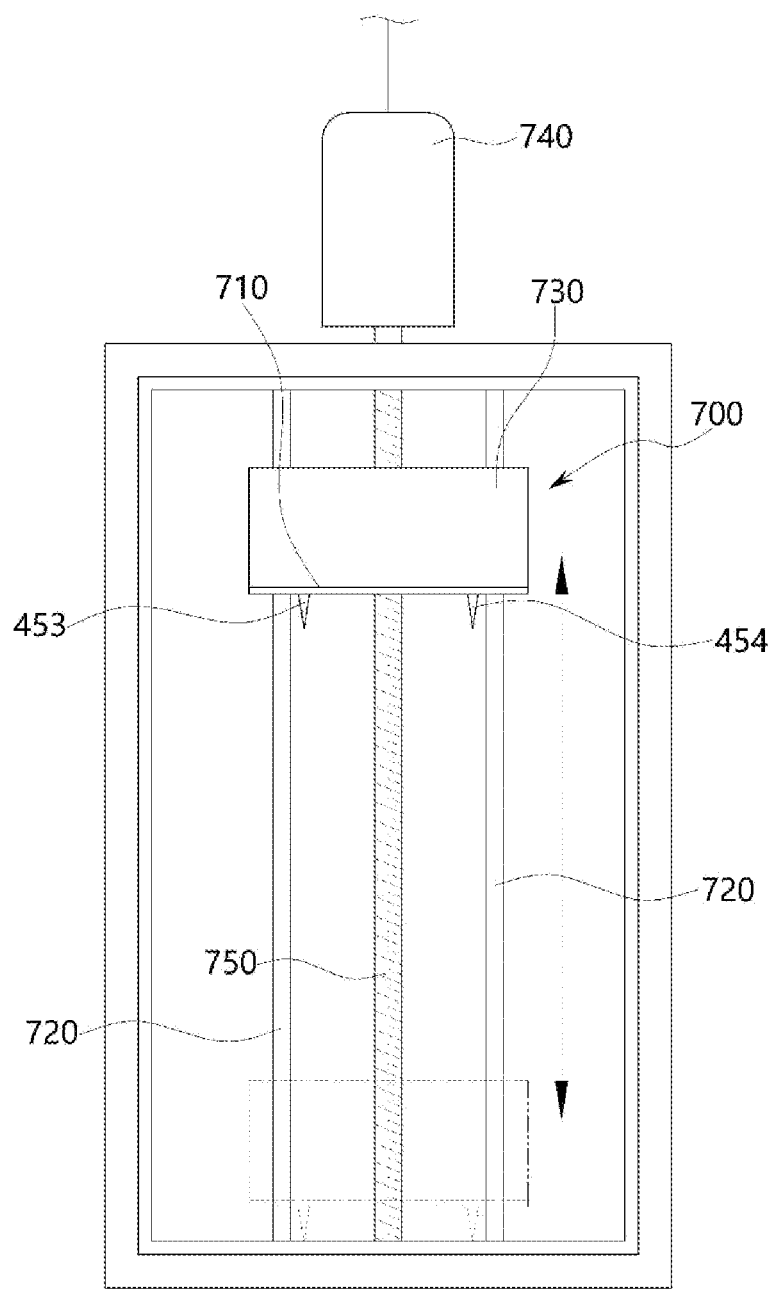
FIG. 4 is a plan view showing a contaminant particle damage part shown in FIG. 3.
Figure 5:
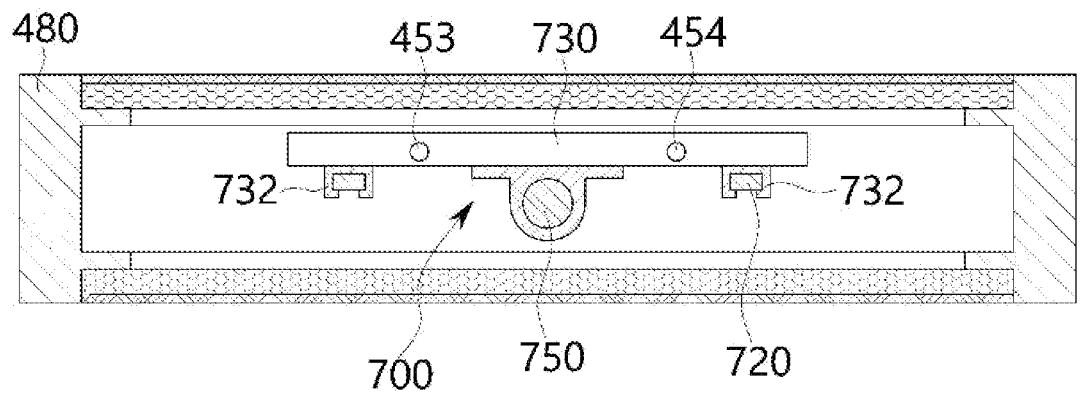
FIG. 5 is the contaminant particle damage part shown in FIG. 4.
Figure 6:
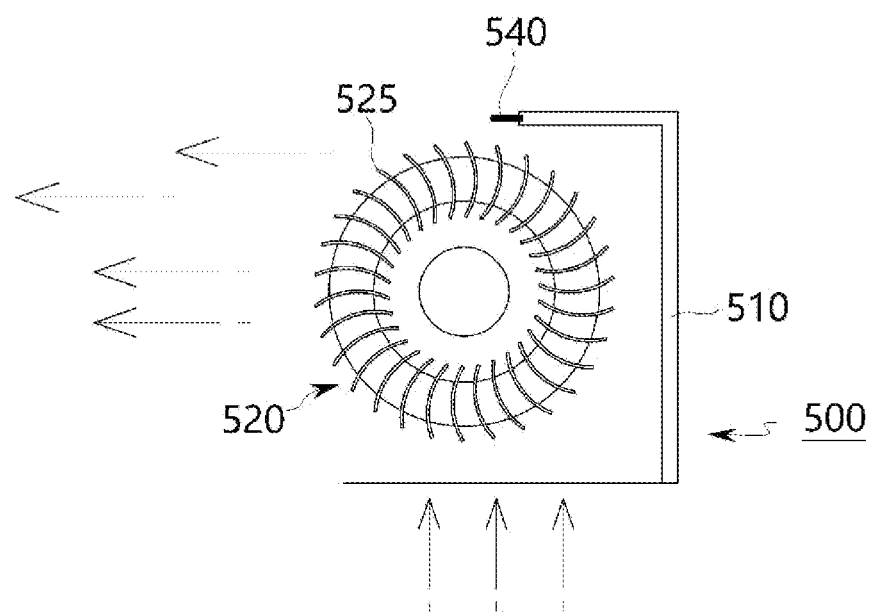
FIG. 6 is a cross-sectional view of an ion-generating part for emitting anions to the outside in FIG. 1 and FIG. 2.
Figure 7:
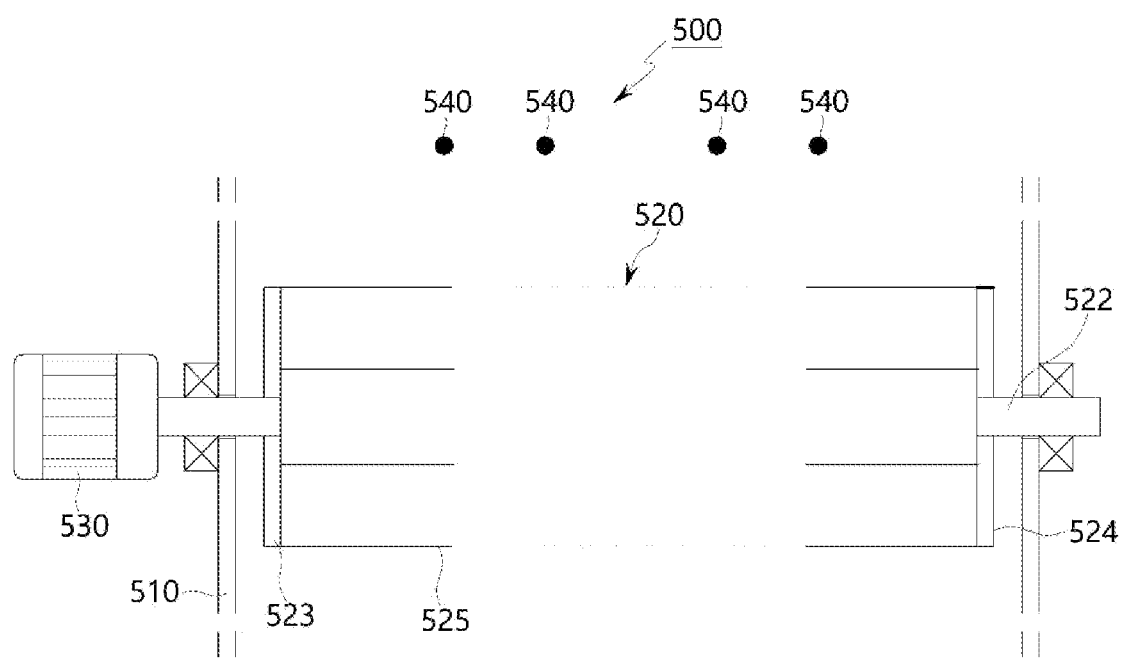
FIG. 7 is a side sectional view of main parts shown in FIG. 6.

Referring to FIG. 3 to FIG. 5, the damage part 450 includes positive and negative electrode members 451, 452 for providing polarities to the first and second metal mesh members 410, 420, positive and negative needle electrodes 453, 454 positioned between the first and second filters 430, 440, and a polarity converter 455 for converting the polarities of the positive and negative electrode members 451, 452 by a switching operation.

The positive electrode member 451 is connected to the first metal mesh member 410, the negative electrode member 452 is connected to the second metal mesh member 420, and the positive and negative needle electrodes 453, 454 are positioned in the space between the first and second metal mesh members 410, 420 and are connected through a line to a power supply that supplies power.

The first and second metal mesh members 410, 420 may be made of a metal material capable of supplying high voltage of 3,000-8,000 V.

The polarity converter 455 supplies power crossing the polarities of the positive and negative electrode members 451, 452 connected to the first and second metal mesh members 410 and 420 through a signal value according to power supply.

Accordingly, when the air passes through the space between the first and second metal mesh members 410, 420, damage is generated to the harmful components passing through the space by switching the polarity converter 455 to change the polarities, wherein if the polarity converter 455 is continuously switched in a regular or irregular manner, repetitive damage is applied to the harmful components.

The anions generated by the damage part 450 encompasses the bacteria and blocks the supply of nitrogen, wherein the hydrogen of a cell membrane is decomposed to be destroyed and thus sterilization is carried out.

At this time, the amount of ions generated by the damage part 450 is about 20 million or more in the space between the first and second metal mesh members 410, 420 such that the ions sterilize bacteria and the like, and the bacteria still surviving after the ion sterilization pass through the metal mesh member 420 and are additionally sterilized by the damage caused by the switching of the polarities that deteriorates the viability of the bacteria.

Meanwhile, the high voltage crossing application process through the damage part 450 will be described hereinbelow.

When the high voltage of 3,000 V or higher is applied to the first and second metal mesh members 410, 420 as shown in the drawings, if bacteria, viruses and the like are allowed to pass through the first metal mesh member 410, the cell membranes thereof are destroyed by the damage due to the high voltage and thus the bacteria, viruses and the like are sterilized.

When the high voltage applied to the first and second metal mesh members 410, 420 is continuously supplied while switching the polarities by crossing the negative and negative electrodes, the high voltage applied to the first and second metal mesh members 410, 420 is continuously switched between the negative polarity and the positive polarity and applies high voltage damage to the passing bacteria by repeatedly applying the negative polarity and the positive polarity to the cell membranes of the passing bacteria, thereby increasing the sterilizing effect.

The air intake fan 300 is a fan for introducing air through the rotation of the fan and it is preferable that at least one or more air intake fans 300 are installed in the space 110 of the body 100, wherein it is preferable that such air intake fans 300 are installed at the upper side of the primary filtering part 200 or at the upper side of the secondary electrostatic filter part 400.

The ion generating part 500 includes a rotation fan 520 rotatably coupled to the inside of a case 510 positioned at the upper side in the space of the body 100 so as to introduce and discharge air, a motor 530 for rotating the rotation fan 520 at one side of the case 510, and four electrode members 540 arranged in the case 510 so as to form electrodes in the air and thus generate ions.

The rotation fan 520 includes rotation plates 523, 524 rotatably coupled through rotation shafts 521, 522 at both inner walls of the case 510, and a plurality of blades 525 respectively having both ends fixed to the corresponding wall surfaces of the rotation plates 523, 524 respectively, wherein the both ends are fixed with an inclination angle such that the air is introduced or discharged during rotation of the rotation plates 523, 524.

Accordingly, as the power is supplied, the power is supplied to the electrode members 540 according to the polarities and the rotation fan 520 is rotated at the same time. Herein, by the rotation fan 520, the inflowing air passes through the four electrode members 540 in the case 510 and is supplied to the outside through the air outlet part 140 together with the anions generated by the electrode members 540, thereby purifying the outside air through the anions.

The air disinfection process of the air sterilizer according to the present invention will be described hereinafter.

In order to disinfect a room, the power is first turned on.

Figure 2:
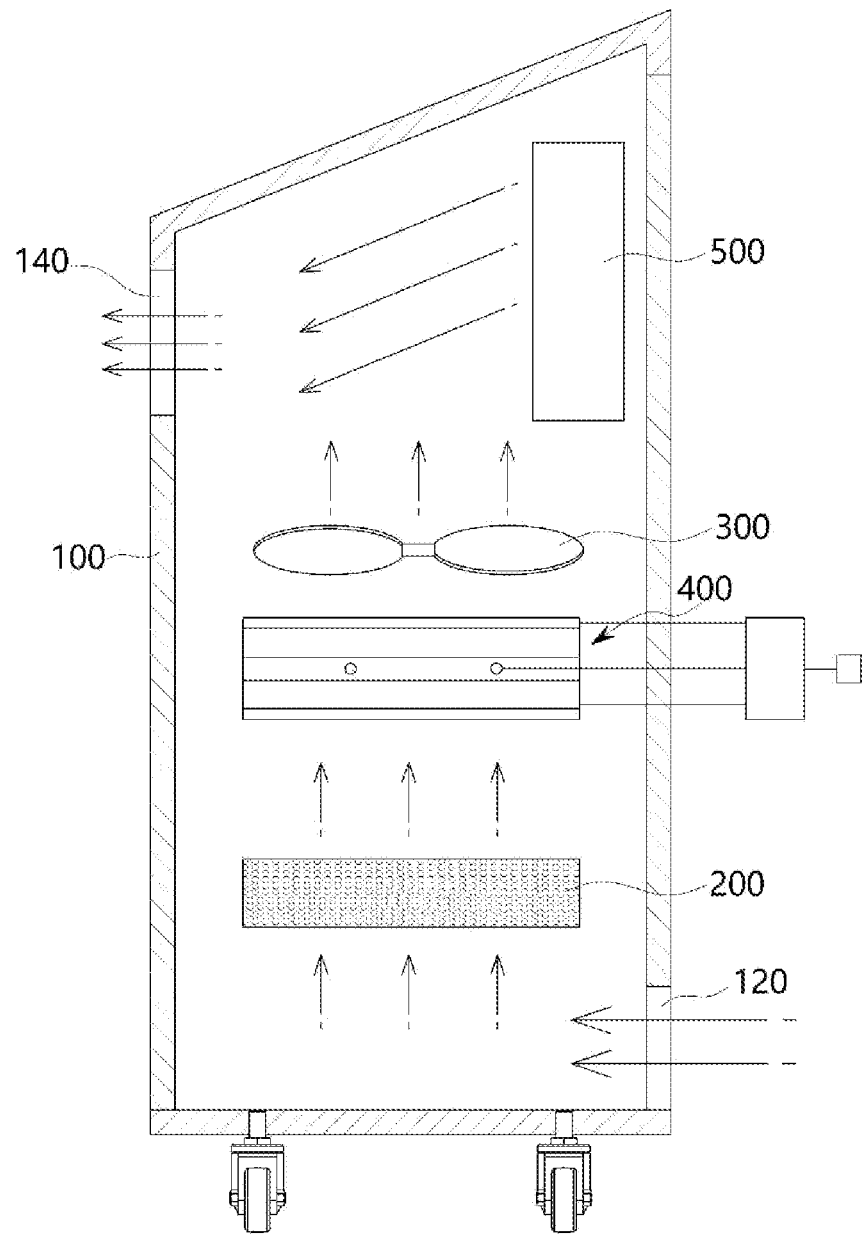
FIG. 2 is a side sectional view showing the air sterilizer shown in FIG. 1.

Then, as shown in FIG. 2, outside air flows into the space 110 of the body 100 through the air inlet part 120 while the air intake fan 300 is rotated. Herein, the inflowing air is filtered by the primary filtering part 200 and subsequently the filtered air passes through the secondary electrostatic filter part 400.

At this time, as the damage part 450 constituting the secondary electrostatic filter part 400 is operated, the first and second metal mesh members 410, 420 convert polarities regularly or irregularly according to signal values, thereby applying damage to bacteria.

After that, the damaged bacteria are weakened in viability, lose the viability through the anions in the weakened state, and are finally sterilized by additional damage while subsequently passing through the second metal mesh member 420.

The sterilized air then is discharged through the air outlet part 140 together with the anions of the ion generating part 500, thereby purifying the outside air.

As another example, as shown in FIG. 3 to FIG. 5, the positive and negative needle electrodes 453, 454 may be movably installed through a guide means 700 between the first and second metal mesh members 410, 420.

The guide means 700 may include a frame member 480 for forming an outer appearance so that the first and second metal mesh members 410, 420 are installed to be spaced apart from each other, a needle holder 710 positioned at one side inner wall of the frame member 480, having the positive and negative electrode needles 453, 454, and connected to a power supply, guide rails 720, of which both ends are fixed to the inner wall of the frame member 480, a slider 730, of which one side is coupled to the needle holder 710 and the other side is coupled to blocks 732 that slide along the guide rails 720, and a rotation screw 750, which is screw-coupled to the slider 730, of which both ends are rotatably coupled to the inner walls of the frame member 480, and of which one side is rotated in the forward or backward direction in accordance with the rotation of a motor driving part 740 such that the slider 730 is moved forward or backward.

This first and second metal mesh members 410, 420 are continuously or irregularly converted in the positive and negative polarities through the polarity converter 455, and the positive and negative needle electrodes 453, 454 move back and forth between the first and second metal mesh members 410, 420 through the slider 730, such that the damage to the moving harmful particles can be caused more greatly.

Although the preferred embodiments of the present invention have been described above, the present invention is not limited to the specific embodiments described above. That is, those skilled in the art will recognize that many changes and modifications can be made to the present invention without departing from the spirit and scope of the appended claims, and all such appropriate changes and modifications should be considered as equivalents falling within the scope of the present invention.

What is claimed is:

1. A air sterilizer for filtering and discharging harmful components from inflowing air, comprising:
- a body having an air inlet part, through which outside air is introduced, and an air outlet part, through which the air filtered inside is discharged;
- a primary filtering part detachably provided in the body and filtering contaminant particles from the inflowing and moving air;
- an air intake fan for allowing the air to inflow through the air inlet part;
- a secondary electrostatic filter part for sterilizing harmful components from the air, which has been filtered through the primary filtering part, by applying continuous and repetitive damage to the harmful components; and
- an ion-generating part for supplying anions to the air, from which the harmful components have been filtered through the secondary electrostatic filter part, so as to allow the air to be discharged to the outside, wherein the secondary electrostatic filter part includes:
- first and second metal mesh members coupled to each other by means of a frame member so as to face each other up and down and have a space therebetween;
- first and second filters positioned in the space between the first and second metal mesh members; and
- a damage part positioned in a space between the first and second filters so as to apply continuous and repetitive damage to the air passing through the space;

wherein the damage part includes:
- positive and negative electrode members for providing polarities to the first and second metal mesh members;
- positive and negative needle electrodes positioned between the first and second filters; and
- a polarity converter for converting the polarities of the positive and negative electrode members by a switching operation.

2. The air sterilizer according to claim 1, wherein the positive and negative electrode needles are installed so as to move between the first and second metal mesh members through a guide means, and the guide means includes:
- a frame member for forming an outer appearance so that the first and second metal mesh members are installed to be spaced apart from each other;
- a needle holder positioned at one side inner wall of the frame member, having the positive and negative electrode needles, and connected to a power supply;
- guide rails, of which both ends are fixed to the inner wall of the frame member;
- a slider, of which one side is coupled to the needle holder and the other side is coupled to blocks that slide along the guide rails; and
- a rotation screw, which is screw-coupled to the slider, of which both ends are rotatably coupled to the inner walls of the frame member, and of which one side is rotated in the forward or backward direction in accordance with the rotation of a motor driving part such that the slider is moved forward or backward.

* * * * *